United States Patent [19]

Dougherty et al.

[11] Patent Number: 4,507,495

[45] Date of Patent: Mar. 26, 1985

[54] PROCESS FOR PRODUCTION OF ETHYL ACRYLATE

[75] Inventors: Edward F. Dougherty, League City; Mark O. Scates, Pearland; James L. Paul, Houston, all of Tex.

[73] Assignee: Celanese Corporation, New York, N.Y.

[21] Appl. No.: 510,846

[22] Filed: Jul. 5, 1983

[51] Int. Cl.$^3$ ................................................ C07C 67/04
[52] U.S. Cl. ................................................... 560/205
[58] Field of Search ................ 560/205, 217, 235, 247

[56] References Cited

U.S. PATENT DOCUMENTS

| | | | |
|---|---|---|---|
| 3,539,621 | 11/1970 | Cipollone et al. | 560/205 |
| 3,686,268 | 8/1972 | Jobert et al. | 560/217 |
| 3,894,076 | 7/1975 | Van Duyne et al. | 560/205 |
| 4,175,089 | 11/1979 | Heiba et al. | 549/326 |

*Primary Examiner*—Natalie Trousof
*Assistant Examiner*—L. Hendriksen
*Attorney, Agent, or Firm*—L. I. Grim; M. Turken

[57] ABSTRACT

In the process of producing ethyl acrylate by the reaction of ethylene and acrylic acid in the presence of sulfuric acid, using phenolic type inhibitors, soluble manganese or cerium salts are additionally utilized.

17 Claims, 1 Drawing Figure

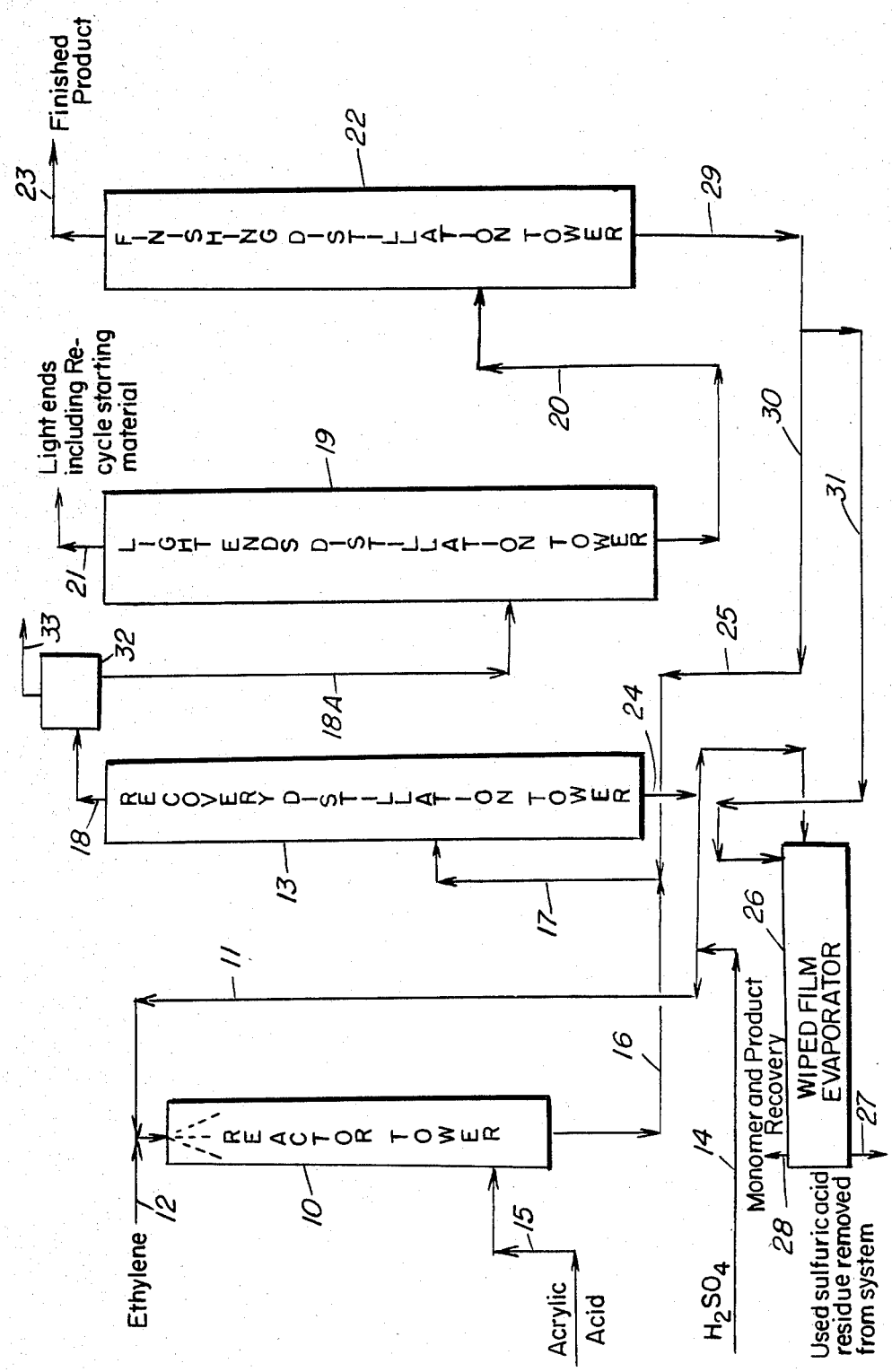

PROCESS FOR PRODUCTION OF ETHYL ACRYLATE

This invention relates to improvements in the process for producing ethyl acrylate by the reaction of ethylene and acrylic acid in the presence of sulfuric acid.

BACKGROUND OF THE INVENTION

Processes for the production of ethyl acrylate by interacting acrylic acid with ethylene in the presence of sulfuric acid are well known; see for example U.S. Pat. No. 3,703,539 issued Nov. 21, 1972 to DiLiddo; U.S. Pat. No. 3,539,621 issued Nov. 10, 1970 to Cipollone et al; and U.S. Pat. No. 3,894,076, issued July 8, 1975 to Van Duyne et al. As described in these and other references, the reaction is believed to involve the formation of intermediate sulfates from the reaction of ethylene with sulfuric acid. These sulfates further react with acrylic acid to form ethyl acrylate. To provide a product in good overall yields with high carbon efficiencies, unreacted ethylene, acrylic acid and the sulfuric acid residue must be recycled to the reactor. Copending application U.S. Ser. No. 182,553 filed Aug. 29, 1980 and assigned to Celanese Corporation describes processing improvements of passing specific product residues to a wiped-film evaporator and the remainder, if any, back to the separation step of the crude ethyl acrylate and a sulfuric acid residue in the ethyl acrylate production from ethylene, and acrylic acid in the presence of sulfuric acid.

In the above processes, the acrylic acid used normally contains inhibitors which prevent undesired polymerization prior to use. The inhibitors commonly used are phenothiazine, methylene blue, phenolic type inhibitors such as hydroquinone, p-methoxyphenols and the like. It is not generally known to use a metal additive in combination with organic inhibitors in acrylic acid. In *Chemical Abstracts* Vol. 74, 1971, 112642V, a Japanese patent (70-35,285) filed June 1, 1967, assigned to Nippon Kayaku, Co. Ltd., describes the mixture of chromium acetate with hydroquinone as a satisfactory inhibitor for acrylic acid and methacrylic acid. In Japanese Patent Publication No. 51-98211, filed Feb. 15, 1975 assigned to Sumitomo Chemical Co. Ltd., the combination of a manganese salt and phenolic type inhibitors provided satisfactory stabilization of acrylic acid. In copending application Ser. No. 06/510,870 entitled "Stabilized Ethylenically Unsaturated Organic Compositions" filed July 5, 1983 and assigned to the same assignee as the present application, describes the use of cerium in combination with other inhibitors as an inhibitor for polymerizable ethylenically unsaturated organic compounds. In this invention, however, improvements are achieved over the above described and known ethyl acrylate production techniques using manganese and cerium ion additives soluble in the reaction mixture.

THE INVENTION

It has been discovered that if soluble metal ions of manganese or cerium are added to the reaction mixture of ethylene, acrylic acid containing phenolic type polymerization inhibitors and sulfuric acid in the production of ethyl acrylate, unexpected improvements in acrylic acid efficiencies to ethyl acrylate and thus improved ethyl acrylate yields are achieved. The preferred way to add the metal ions is during the acrylic acid processing, prior to the ethylene-acrylic acid reaction step.

The accompanying drawing is a simplified schematic flow sheet exemplifying the preparation of ethyl acrylate from ethylene and acrylic acid in the presence of substantially anhydrous sulfuric acid showing the use of a wiped-film evaporator for removal of a portion of the spent sulfuric acid residue.

To achieve the improvements of this invention, the process for producing ethyl acrylate, schematically represented in the drawing can be used. This process includes a combination of substantially anhydrous sulfuric acid medium supplied through line 11 and ethylene supplied through line 12 is sprayed into reactor tower 10 and mixed. The sulfuric acid medium is comprised of sulfuric acid residue or bottoms from the product recovery distillation tower 13 along with make-up sulfuric acid added through line 14. The sulfuric acid residue (sometimes referred to in the industry as "black acid") recovered from the recovery distillation tower 13 is a mixture of various compounds and contains sulfuric acid, unreacted acrylic acid, some small amounts of ethyl acrylate and various other compounds.

In the reactor tower 10, the main reaction of concern is the liquid phase reaction of ethylene-enriched liquid with sulfuric acid to give various intermediate sulfate salts, such as ethyl hydrogen sulfate and diethyl sulfate, which will then further react with acrylic acid, supplied through line 15 to form ethyl acrylate.

Adequate mixing of the reaction mixture in the reaction tower 10 can be obtained by mechanical stirring or recycle of the reaction products. (Neither mixing techniques are shown in the drawing). The reactants' residence time in the reactor tower 10 must be sufficient to obtain substantially (preferably at least a 80% completion) complete reaction of ethylene. Temperatures in the reaction tower should be maintained within the range of about 100° C. to about 150° C., preferably 110° C. to 130° C. and the pressure should be maintained within the range of about 100 to about 300 psig, preferably 130 to 200 psig. In this invention the metal ions of manganese or cerium soluble in the reaction mixture can be added separately in an additional line (not shown to the reactor tower 10) or can be added with the acrylic acid containing polymerization inhibitors, preferably, the metal ions are added to the acrylic acid during acrylic acid processing prior to the addition of the acrylic acid to the reactor tower through line 15.

Any type of manganese or cerium compound which is soluble in the acrylic acid or reaction mixture can be used in this invention. Suitable manganese compounds include, among others manganous acetate, manganous propionate, manganous nitrate, manganous oxide, manganous hydroxide, manganous chloride, manganous phosphate, manganous perchlorate and the like. Suitable cerium compounds include, among others, ceric ammonium nitrate, cerous acetate, cerous ammonium nitrate, cerous ammonium sulfate, cerous benzoate, cerous nitrate, cerous oxalate and the like. The amount of metal ions used are from about 5 parts per million to about 5,000 parts per million, preferably from about 25 to about 500 parts per million of the total reaction mixture.

The type of acrylic acid inhibitor used herein include known inhibitors preferably the phenolic type inhibitors such as dihydroxybenzene derivatives such as hydroquinone, catechol, resorcinol, dihydroxyxylene; methoxyphenols such as guaiacol and p-methxyphenol (methyl ether of hydroquinone); pyrogallol; methylpyrogallol; cresols; phenol; xylenols; 4,4-thiobis-6-tertiarybutyl-3-methylphenol and the like. The amounts of phenol type inhibitors used in this invention are from about 5 parts per million to about 5,000 parts per million, preferably from about 25 parts per million to about 500 parts per million based on the total reaction mixture. The inhibitors can be added to the reactor tower 10 in combination with the acrylic acid or added separately, if desired. Additional inhibitors and metal ions can be carried with the sulfuric acid residue from the recovery distillation tower 13 through line 11 to the reactor tower 10.

The reaction products from the reactor tower 10 are withdrawn through line 16 and passed through a pressure reduction valve (not shown) and thence to the recovery distillation tower 13. The distillation section of the recovery distillation tower may be of conventional design, and may contain packing, sieve type trays or dual flow trays. The distillation section should contain an equivalent of at least four theoretical trays. A vacuum is maintained in the recovery distillation tower 13 by conventional means so that the pressure is less than about 200 mm of mercury absolute, and preferably within the range of 20 to 150 mm of mercury absolute. The still pot temperature should be maintained within the range of about 100° C. to about 170° C., preferably 110° C. to 130° C. and the still head temperature within the range of about 28° C. to about 45° C., preferably 30° C. to 40° C.

The feed line 17 to the recovery distillation tower 13 is directed preferably to the lower third, and more preferably to the base of the tower. In the recovery distillation tower 13, the light ends of crude ethyl acrylate in line 18, comprising mainly ethyl acrylate, unreacted ethylene and other uncondensables, are separated from the liquid material in the gas liquid separator 32 and are removed overhead through line 33. The uncondensed ethylene and inerts are vented through the vacuum compressor. The liquids are passed through line 18A to the light ends distillation tower 19 (of conventional distillation design). Partially purified ethyl acrylate product is removed as bottoms through line 20. A stream comprising of sulfur dioxide, diethyl ether and ethylene are removed from the light ends distillation tower 19 through line 21 and ethylene may be disposed of or recycled (not shown) to the reactor tower 10 as desired, although if recycled a scrubbing to remove sulfur oxides is recommended. The partially purified ethyl acrylate product recovered through line 20 is further treated by fractionation in the finishing distillation tower 22 to obtain, through line 23, a substantially pure ethyl acrylate having a purity greater than 95 percent, preferably about 99.9 percent or higher.

In operating the recovery distillation tower 13, the residence time of the reaction products in the base of the tower should be as low as possible because at temperatures required in the reboiler for vaporization some polymerization may occur.

The sulfuric acid residue or black acid stream referred to above, containing sulfuric acid, intermediate sulfates, unreacted acrylic acid and the like is removed as bottoms residue from the recovery distillation tower 13 through line 24. A blowdown of a minor portion of the bottoms stream or sulfuric acid residue which is approximately 1 to 5 percent by weight of the total sulfuric acid residue is taken by means of line 25 so as to prevent the buildup of impurities in the system. The remaining major portion of the sulfuric acid residue can be recycled through line 11 to the reactor tower 10 in combination with ethylene.

This minor portion of the sulfuric acid residue is passed through line 25 to a horizontal wiped-film evaporator 26 which heats the sulfuric acid residue to temperatures in the range from about 300° F. to about 360° F., and preferably 325° F. to 350° F. in the initial portion of the wiped-film evaporator 26. At the last or withdrawal section(s) of the wiped-film evaporator 26, the spent sulfuric acid residue is cooled to temperatures in the range from about 230° F. to about 280° F., and preferably 240° F. to 270° F., for removal from the system through line 27. During the treatment of the sulfuric acid residue for the process of this invention, the wiped-film evaporator 26 is maintained under reduced pressure in the range from about 40 to about 150 mm of mercury absolute and preferably in the range from about 50 to 80 mm of mercury absolute. Ethyl acrylate and acrylic acid can be recovered through line 28 from the wiped-film evaporator 26. The preferred procedure for the ethyl acrylate and acrylic acid removed from the wiped-film evaporator is to recycle these products to the recovery distillation tower 13 for reprocessing.

Although not shown on the drawing, the addition of a polymerization inhibitor is generally desirable when producing or purifying ethyl acrylate. Such inhibitors are known, and can be materials soluble in the reaction medium or soluble in the product obtained from the recovery distillation tower. Suitable polymerization inhibitors include hydroquinone, phenothiazine, the methyl ether of hydroquinone, quinone and the like. The polymerization inhibitor can be introduced to the reaction vessel in the used sulfuric acid residue or through any other convenient part of the system. It is required that the inhibitor be added to lines 18, 21 and 23. The inhibitor can be added in line 18 from which it is carried out through to the light ends distillation tower 19, then into the finishing distillation tower 22 and into the residue of the finishing distillation tower 22.

The ethyl acrylate product residue of the finishing distillation tower 22 can be passed through lines 29 and 30 to line 17 back into the recovery distillation tower 13 and finally combined with the sulfuric acid residue to be recycled through line 24 and back to the reactor tower 10. An alternative procedure includes passing all or a portion of the ethyl acrylate product residue through lines 29 and 31 to the wiped film evaporator 26. A portion of ethyl acrylate product residue can be passed through to both the wiped film evaporator 26 and the reactor tower 10.

The wiped-film evaporator which can be used in the process of the present invention can be a vertical or horizontal unit. For this invention, a horizontal unit is preferred. Typical of the units that can be used and are known are the types described in a three part report in *Chemical Engineering*, Sept. 13, 1965, pages 175-190, entitled "Agitated Thin-Film Evaporators". The one essential criterion of the wiped-film evaporator used in this process is the capability of cooling the latter section of the evaporator to provide a residue having specific temperature ranges as described herein. A problem in the treatment of the combination of the viscous sulfuric acid residue and the ethyl acrylate product residue, is the foaming of the residue in the latter section(s) of the wiped-film evaporator on heating at temperatures in the range from about 300° F. to about 360° F. These temperatures are needed to effectively and efficiently separate ethyl acrylate and acrylic acid from the sulfuric acid residue. The foaming of the treated residue can be so severe that the foamed material can back up into the purification system requiring the shut down of the process. This foaming can be substantially eliminated by cooling the last or withdrawal section(s) of the wiped-film evaporator to temperatures in the range from about 230° F. to about 280° F.

The following examples illustrate the process of this invention.

EXAMPLES 1 and 2

Referring to the description of the drawing and using the process described, ethylene via line 12 and acrylic acid via line 15 are added to reactor 10 containing 12,000 gallons of sulfuric acid, 4 weight percent phenothiazine and 5000 parts per million hydroquinone.

Example 1 produces ethyl acrylate without the presence of manganese metal ions. Example 2 using the above-described reactor contents adds manganous acetate in amounts wherein the reaction mixture contains 340 parts per million manganese metal ions. The manganese metal ions are introduced into the reactor via acrylic acid containing the soluble manganese metal ions.

The wiped-film evaporator was operated under reduced pressure of 100 mm absolute. The temperatures of the oil used in the initial sections of the wiped-film evaporator were maintained in the range from 330° F. to 370° F. The coolant in the last or withdrawal sections of the wiped-film evaporator was hot condensate (steam) maintained at temperatures in the range from 250° F. to 270° F.

The following table of comparative data illustrates the differences in ethyl acrylate production with and without the use of manganese metal ions:

Table of Comparative Data

|  | Example 1 Process without Mn | Example 2 Process with Mn |
|---|---|---|
| Ethylene fed to reactor | 3,795 lbs/hr. | 4262 lbs/hr. |
| Acrylic acid fed to reactor | 10,008 lbs/hr. | 10,607 lbs/hr. |
| Manganese metal ions (ppm total reaction mixture) fed as manganous acetate | 0 | 340 |
| Reaction temperature Reaction tower 10 | 272° F. | 272° F. |
| Recycle Rate from Recovery distillation tower 13 to Reactor tower 10 | 400 gallons per minute | 430 gallons per minute |
| Total Ethyl Acrylate Recovery | 11,541 lbs/hr. | 12,791 lbs/hr. |
| Ethylene efficiency to ethyl acrylate | 85.2% | 84.1% |
| Acrylic Acid efficiency to ethyl acrylate | 83.0% | 86.8% |
| Reactor, Vol gallons | 30,000 | 30,000 |
| Blowdown (used sulfuric acid residue removed from system through line 27). | 3,410 lbs/hr. | 3,086 lbs/hr. |
| Ratio lbs ethyl acrylate per lbs Blowdown | 3.3 | 4.14 |

The process of the present invention as represented in Example 2 using manganese metal ions in the ethylene-acrylic acid-sulfuric acid reaction to produce ethyl acrylate, provides an 3.8 percent improvement in acrylic acid efficiency to ethyl acrylate compared to the reaction process of Example 1 without manganese metal ions being present. In both examples, the ethylene efficiency to ethyl acrylate are similar. Under equivalent conditions, the process of Example 2 (process of this invention) produces 1,250 pounds per hour or 30,000 pounds per day more ethyl acrylate than the process of Example 1 (no manganese metal ions present).

In Example 2 wherein the manganese ions are present in the reaction, there is a marked reduction of the used sulfuric acid residue blowdown (line 27) compared to Example 1 which did not have manganese metal ions present. The ratio of ethyl acrylate production to sulfuric acid residue blowdown is greater for Example 2 vs. Example 1.

What is claimed is:

1. In a process for the production of ethyl acrylate by reacting ethylene and acrylic acid in the presence of sulfuric acid, the improvement comprising adding metal ions selected from the group consisting of soluble manganese and cerium to the reaction mixture.

2. The process of claim 1 wherein the metal ions present are from about 5 parts per million to about 5000 parts per million of the total reaction mixture.

3. The process of claim 2 wherein the metal ions present are from about 25 parts per million to about 500 parts per million of the total reaction mixture.

4. The process of claim 3 wherein manganous acetate is added to the reaction mixture.

5. The process of claim 3 wherein cerous acetate is added to the reaction mixture.

6. The process of claim 3 wherein ceric ammonium nitrate is added to the reaction mixture.

7. The process of claim 1 wherein a phenolic type polymerization inhibitor combined with the metal ions is added to the reaction mixture.

8. The process of claim 7 wherein the metal ions present are from about 5 parts per million to about 5,000 parts per million of the total reaction mixture and from about 5 parts per million to about 5,000 parts per million of a phenolic type inhibitor of the total reaction mixture.

9. The process of claim 7 wherein the metal ions present are from about 25 parts per million to about 500 parts per million of the total reaction mixture and from about 25 parts per million to about 500 parts per million of a phenolic type inhibitor based on the total reaction product.

10. The process claim 9 wherein the metal ion is manganese and the phenolic type inhibitor is hydroquinone.

11. The process of claim 9 wherein the metal ion is manganese and the phenolic type inhibitor is p-methoxy phenol.

12. The process of claim 9 wherein the metal ion is manganese and the phenolic type inhibitor is catechol.

13. The process of claim 9 wherein the metal ion is manganese and the phenolic type inhibitor is guaiacol.

14. The process of claim 9 wherein the metal ion is cerium and the phenolic type inhibitor is hydroquinone.

15. The process of claim 9 wherein the metal ion is cerium and the phenolic type inhibitor is p-methoxy phenol.

16. The process of claim 9 wherein the metal ion is cerium and the phenolic type inhibitor is catechol.

17. The process of claim 9 wherein the metal ion is cerium and the phenolic type inhibitor is guaiacol.

* * * * *